(12) United States Patent
Ihlenfeldt et al.

(10) Patent No.: US 6,916,616 B2
(45) Date of Patent: Jul. 12, 2005

(54) STABILIZED AQUEOUS NUCLEOSIDE TRIPHOSPHATE SOLUTIONS

(75) Inventors: Hans-Georg Ihlenfeldt, Iffeldorf (DE); Axel Schmidt, Munich (DE); Klaus Muhlegger, Polling (DE); Volker Leitenberger, Seeshaupt (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 10/025,826

(22) Filed: Dec. 19, 2001

(65) Prior Publication Data

US 2002/0119534 A1 Aug. 29, 2002

Related U.S. Application Data

(63) Continuation of application No. 09/308,034, filed as application No. PCT/EP97/06276 on Nov. 11, 1997, now abandoned.

(30) Foreign Application Priority Data

Nov. 14, 1996 (DE) .......................................... 196 47 055

(51) Int. Cl.[7] .......................... C12Q 1/68; C12P 19/34; C07H 21/04
(52) U.S. Cl. ............................ 435/6; 435/89; 435/91.1; 435/91.2; 435/91.5; 536/23.1; 536/24.63; 536/24.33
(58) Field of Search ............................ 435/6, 89, 91.1, 435/91.2, 91.5, 87; 536/23.1, 24.3, 24.33

(56) References Cited

U.S. PATENT DOCUMENTS

| | | | | |
|---|---|---|---|---|
| 4,965,188 A | * | 10/1990 | Mullis et al. ................... | 435/6 |
| 5,432,065 A | | 7/1995 | Fuller ......................... | 435/91.1 |
| 5,643,723 A | * | 7/1997 | Persing et al. .................. | 435/6 |
| 5,811,072 A | | 9/1998 | Price et al. .................. | 424/1.73 |
| 5,935,825 A | * | 8/1999 | Nishimura et al. ......... | 435/91.2 |

FOREIGN PATENT DOCUMENTS

| | | | | |
|---|---|---|---|---|
| EP | 0632134 A2 | 1/1995 | ............ | C12Q/1/68 |
| EP | 0751226 A2 | 1/1997 | ............ | C12Q/1/68 |
| FR | 4078 M | 4/1966 | | |
| WO | WO 92/03556 | 3/1992 | ............ | C12N/15/54 |
| WO | WO 96/14405 | 5/1996 | ............ | C12N/15/00 |
| WO | WO98/21362 | 5/1998 | ............ | C12Q/1/68 |

OTHER PUBLICATIONS

Ausubel, F. M., "Current Protocols in Molecular Biology," 1987, John Wiley & Sons, Inc., XP002062215, pp. 3.4.1–3.4.3.
GIBCO BRL Catalogue & Reference Guide, 1992, pp. 298–300.
Perkin Elmer Cetus (catalog, 1988) "GeneAmp DNA Amplification Reagent Kit".
Promega catalog (1992–1993, p. 170 and web site).
Promega website (http://egi.promega.com/catalog/catinfo.asp?idx=1018).
Sambrook et al., "Molecular Cloning: A Laboratory Manual." 1992, 10.6–10.17 and 13.3–13.6.

* cited by examiner

*Primary Examiner*—BJ Forman
(74) *Attorney, Agent, or Firm*—Roche Diagnostics; Marilyn L. Amick

(57) ABSTRACT

The invention concerns stable aqueous solutions containing one or several nucleoside triphosphates wherein the respective solution has a pH value of more than 7.5 and contains no additional substances with a stabilizing effect. The nucleoside triphosphate solutions are used in particular for DNA synthesizing reactions such as e.g. RT-PCR, cycle sequencing, random priming and nick translation. One of the most important applications of such solutions containing deoxy-nucleoside triphosphates (d-NTP) is their use in the polymerase chain reaction (PCR).

9 Claims, 16 Drawing Sheets

Decrease of d-GTP

Decrease of d-CTP

Decrease of d-TTP

Figure 1:
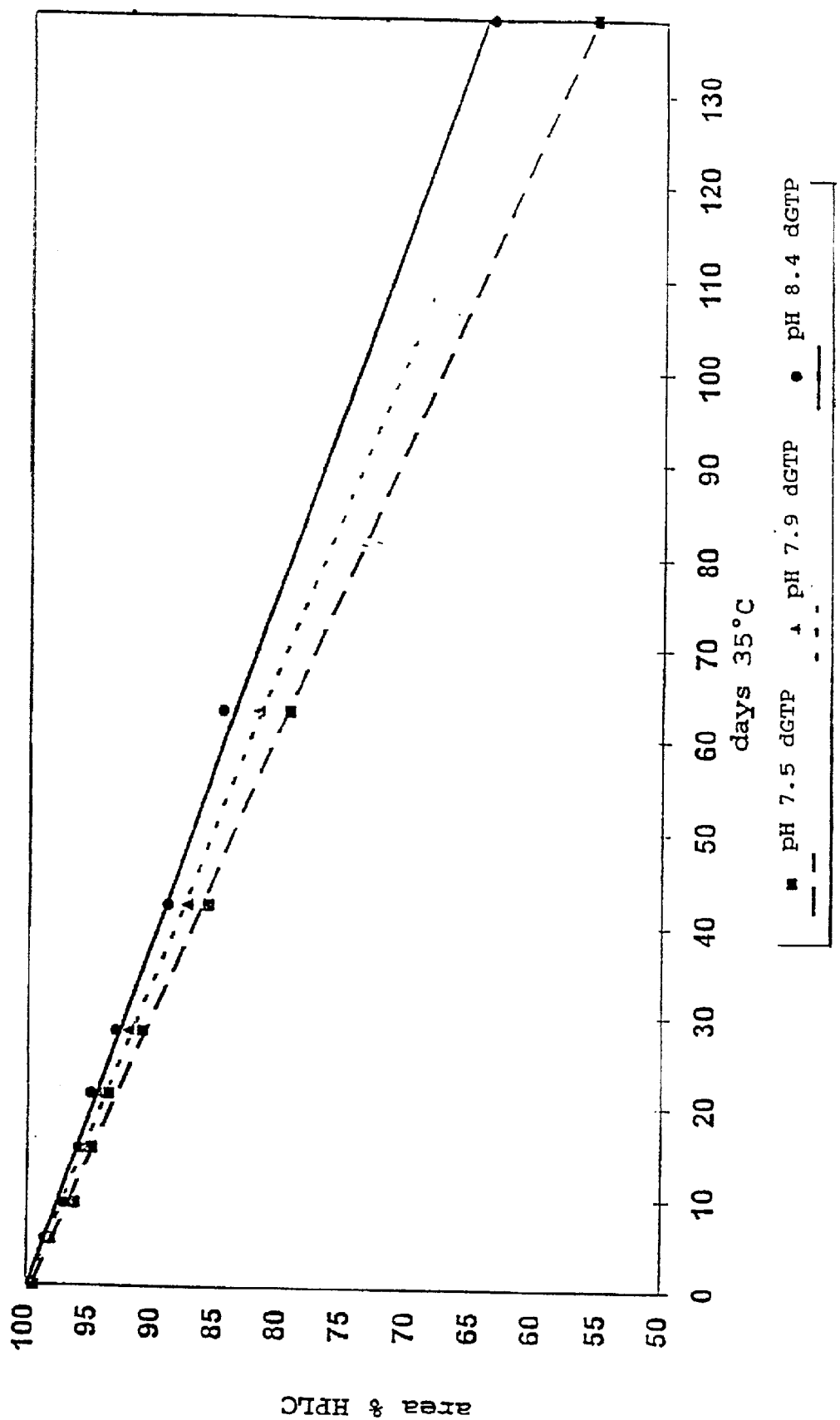

Decrease of d-ATP pH optimum of d-NTPs
(content of triphosphate after 35 days 35°C)

pH stability UTP stability UDP stability ATP stability ADP stability 7-deaza-d-GTP stability 7-deaza-d-GTP Stability dATP with dilution Stability dATP Stability dCTP

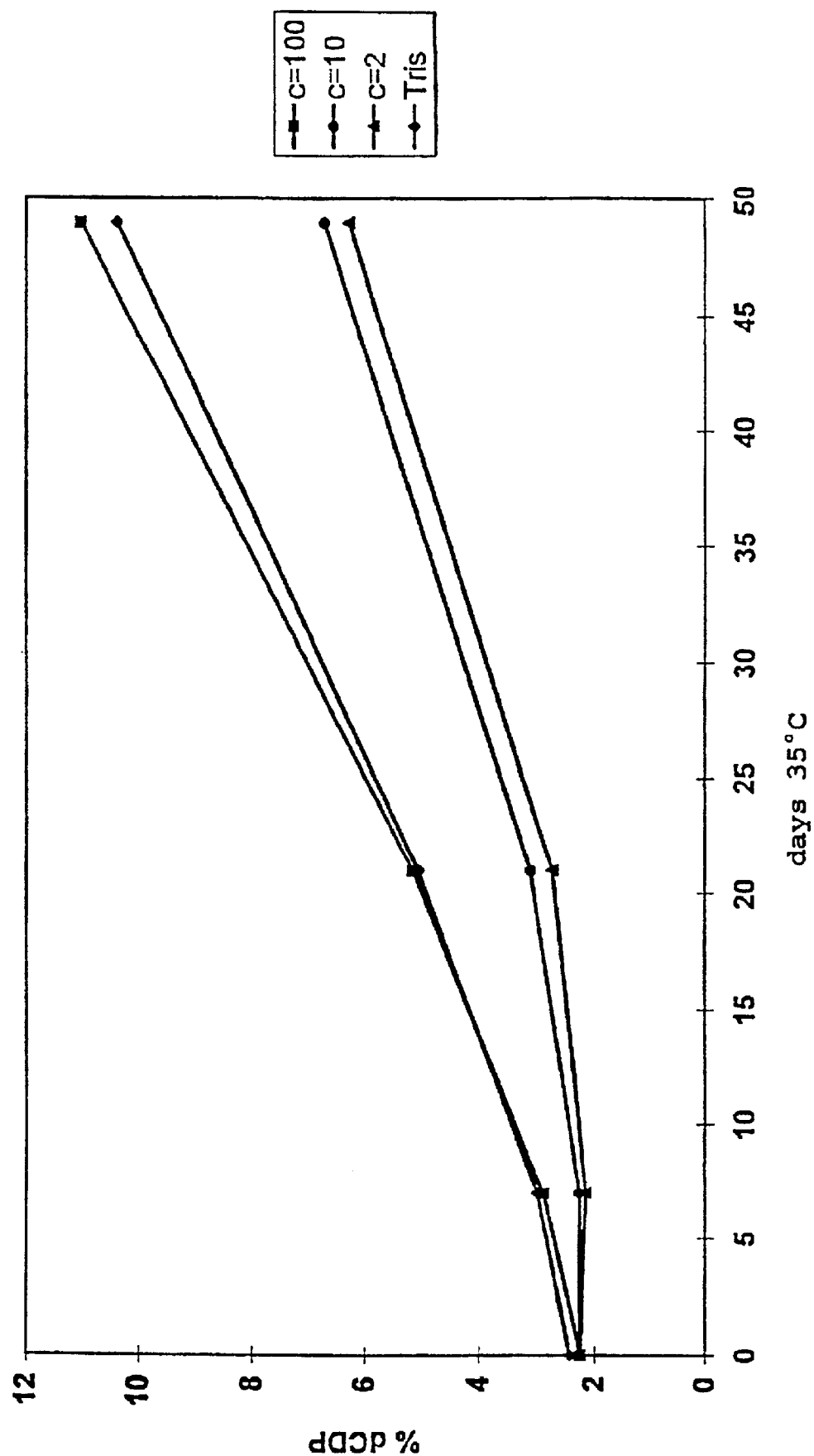

STABILIZED AQUEOUS NUCLEOSIDE TRIPHOSPHATE SOLUTIONS

This application is a continuation of application Ser. No. 09/308,034, filed Nov. 19, 1999 now abandoned.

The invention concerns stable aqueous solutions containing nucleoside triphosphates in which the solution has a pH value above 7.5.

Nucleoside triphosphates (NTP) such as ribonucleoside, deoxynucleoside and dideoxynucleoside triphosphates have a variety of uses in the field of biochemistry and molecular biology. Most of the applications relate to reactions which synthesize or replicate DNA and RNA such as the reverse transcriptase polymerase chain reaction (RT-PCR), cycle sequencing and nick translation. In the case of RT-PCR, DNA chains are synthesized in the 5'-3' direction by for example reverse transcriptase whereby an RNA strand serves as the template. Certain NTPs such as dideoxynucleoside triphosphates (dd-NTP) can be used as chain terminators in the sequencing of DNA. One of the most important applications of deoxynucleoside triphosphates (d-NTP) is their use in the polymerase chain reaction (PCR). In this application it is absolutely essential that the NTP solutions are stable above all during storage. The d-NTPs (d-ATP, d-CTP, d-GTP, d-TTP, d-UTP among others) are usually stored as Na or Li salts and typically at concentrations of 0.1 mol/l and are commercially available in this form. As a rule the pH values are physiological pH values i.e. between ca. 7.0 and 7.5.

A disadvantage of the current, i.e. commercially available, NTP solutions is in particular the instability of the NTPs during storage or thermal stress. The NTPs have a tendency to decompose over time to form the corresponding diphosphates and mono-phosphates. The triphosphate content decreases especially at higher temperatures. The triphosphate content already decreases by ca. 2–3% within ten days at a pH value of ca. 7.5 and a temperature of 35° C. In contrast at room temperature the triphosphate content is observed to decrease by only ca. 1% after six weeks. Hence the decomposition of the triphosphates in aqueous solution limits the shelf life of the NTP solutions. Consequently the suppliers of d-NTPs for example only guarantee a shelf life of 12 months for dNTP solutions. However, there is a need for aqueous solutions which only contain dNTP and this at high concentrations and which have a longer long-term stability than the presently available solutions.

Attempts to improve the stability of triphosphates have up to now merely related to corresponding adenosine triphosphate solutions. The stability of the adenosine triphosphate was examined in relation to the pH value. The presence of stabilizers was described as being absolutely essential in accordance with the state of the art. Thus the stability of adenosine triphosphate in aqueous solution at a pH value of preferably 8.3 to 9.2 is described as being optimal in the presence of EDTA (JP 64/003444). In the presence of stabilizers such as guanidine/amino-guanidine or creatinine a pH value of 9 to 10 (JP 71/038270 and JP 71/033592), in the presence of methionine as a stabilizer a pH value of preferably 9 to 10.5 (JP 67/019115), in the presence of the stabilizers phosphate and sorbitol/mannitol/glycerol/benzyl alcohol/PEG a pH value of 8 to 11 (JP 67/015115) and in the presence of glycerol/$H_3PO_4$ a pH value of 3.7 (FR4078) is described. However, the presence of stabilizers in d-NTP solutions can be critical for many applications or cause interference.

Hence the object of the present invention was to provide a stabilized aqueous solution containing NTPs without the addition of any stabilizers.

The object was achieved according to the invention by the aqueous NTP solutions having a pH value of above approximately 7.5. These nucleotide triphosphates include ribonucleoside triphosphates, deoxynucleotide and dideoxynucleotide triphosphates wherein the five naturally occurring as well as modified bases such as isoguanine, deaza compounds and derivatives thereof come into consideration as bases. Furthermore the nucleoside triphosphates can be labelled with reporter groups. As a rule the solutions according to the invention have a pH value in a range of more than 7.5 to a maximum of 11. A pH value of ca. 8 to 10 proved to be particularly advantageous. The pH value can be set by adding a base (e.g. NaOH, KOH, LiOH) as well as by adding a buffer (e.g. Tris buffer, Na carbonate buffer, phosphate buffer).

The concentration of the NTP solution is preferably between ca. 2 mmol/l and 200 mmol/l. A concentration of the NTPs of ca. 100 to 150 mmol/l is particularly preferred.

Stable d-NTP solutions are a particularly important feature of this invention. The stability of these solutions appears to be advantageous especially with regard to an application in the polymerase chain reaction. As a rule the pH value of the d-NTP solution is above ca. 7.5 and below ca. pH 11. A pH value between ca. 8 and 10 proved to be particularly advantageous. The concentration of the stable d-NTP solution is between 2 mmol/l and 200 mmol/l. A concentration of the d-NTPs of 100 to 150 mmol/l is particularly preferred.

It has surprisingly turned out that the stability of the NTPs in aqueous solution at pH values of more than 7.5 and without the addition of any stabilizers is higher than in the previously known solutions which have a pH value of ca. 7.0 to 7.5. The stability of the d-NTPs in aqueous solution reaches an optimum at a pH value of ca. 8 to 10. The increase of the pH value does not cause any additional degradation reactions i.e. the pattern of the degradation products remains unchanged at the pH values according to the invention. Surprisingly the degradation reactions proceed considerably more slowly at higher pH values such as for example 8.3 than at physiological pH values such as for example 7.5.

Hence it has turned out that at increased pH values no by-products are formed at all which could impair the use of the d-NTPs e.g. for the PCR reaction. Even after ca. 90 days at a temperature of 35° C. the PCR function test is positive. The higher pH value is uncritical for the PCR itself since most PCR amplifications are carried out in any case at pH values of more than 8.0. Hence for example aqueous d-NTP solutions which have a pH value of more than ca. 7.5 and less than/equal to ca. 11 proved to be stable on the one hand and advantageous for use in the PCR reaction. In this case a pH value of the d-NTP solution between 8 and 10 proven to be particularly advantageous.

The stable NTP solutions according to the invention can be used for all DNA and RNA synthesizing and DNA and RNA replicating reactions. In particular the stable NTP solution according to the invention can also be used for RT-PCR, for nick translation, random priming and for sequencing (cycle sequencing). Furthermore the stable NTP solutions according to the invention proved to be advantageous with regard to a longer duration of use of the NTPs. That means that the stable solutions according to the invention can be stored for a considerably longer period than the previously used d-NTP solutions.

FIGURE LEGENDS

FIG. 1: Decrease of the d-GTP content The decrease of the d-GTP concentration at a temperature of 35° C. was monitored over a period of 140 days at pH values of 7.5, 7.9 and 8.4.

Figure 2:
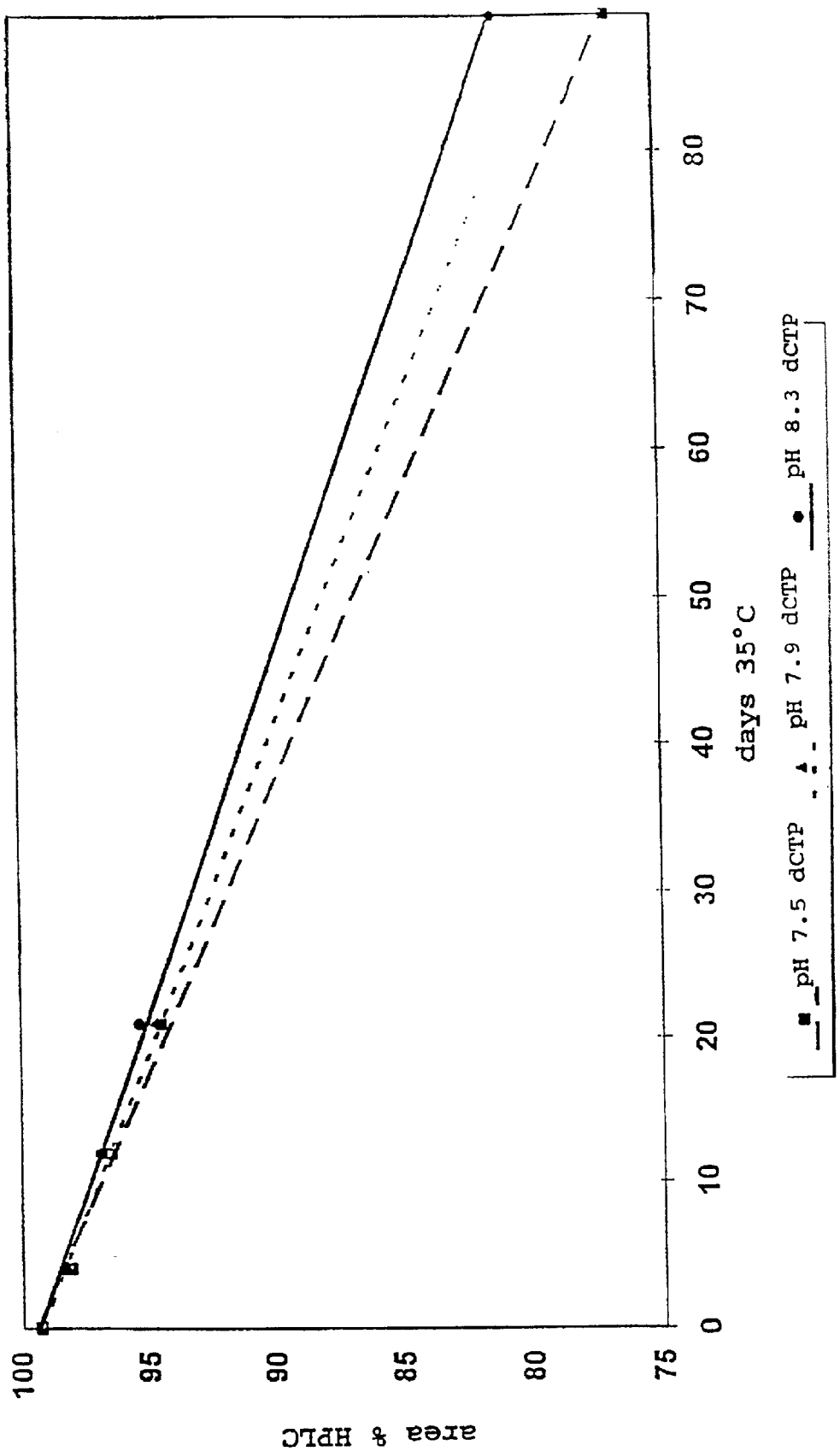

FIG. 2: Decrease of the d-CTP content The decrease of the d-CTP concentration at a temperature of 35° C. was monitored over a period of 90 days at pH values of 7.5, 7.9 and 8.3.

Figure 3:
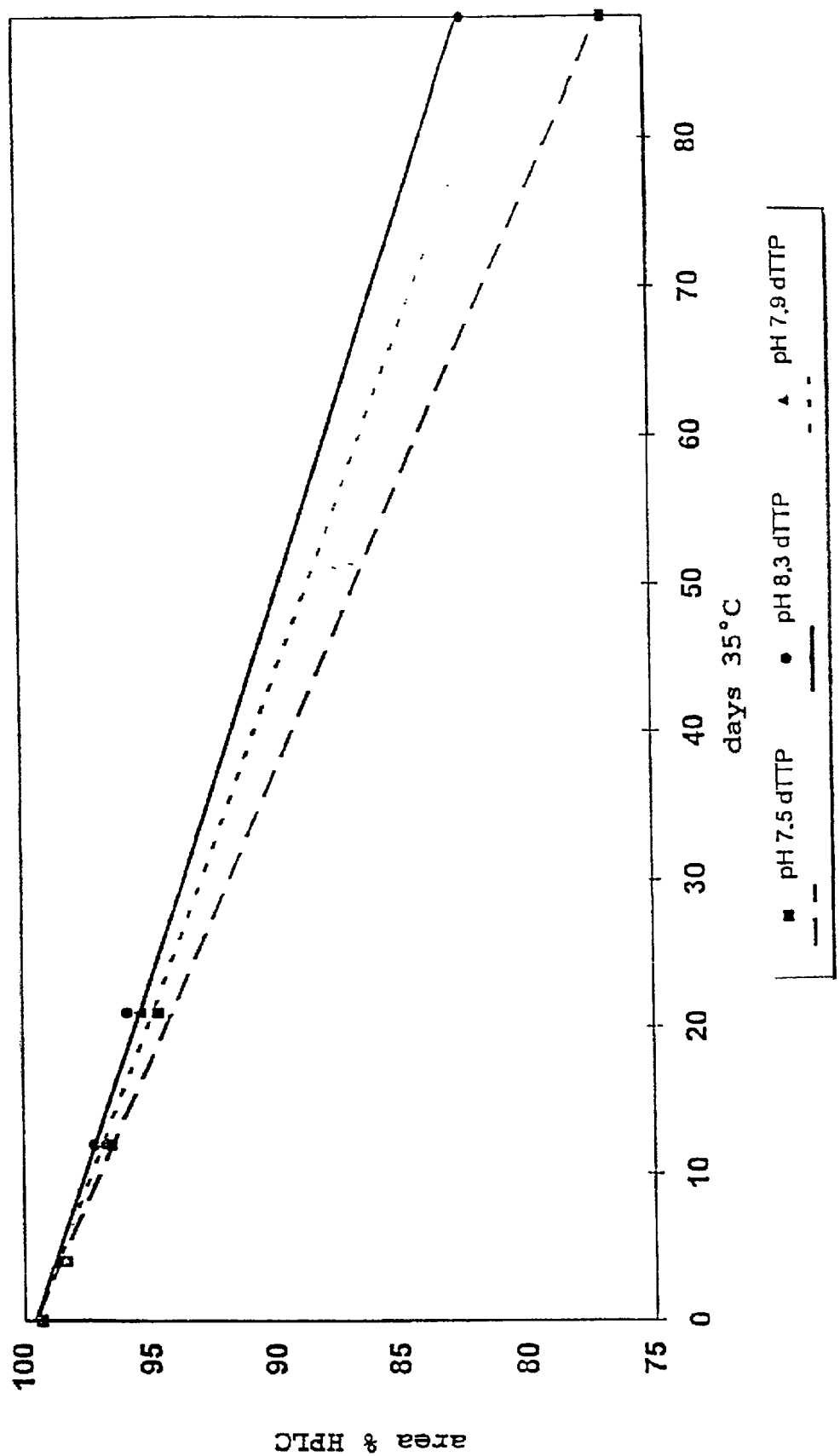

FIG. 3: Decrease of the d-TTP content The decrease of the d-TTP concentration at a temperature of 35° C. was monitored over a period of 90 days at pH values of 7.5, 7.9 and 8.3.

Figure 4:
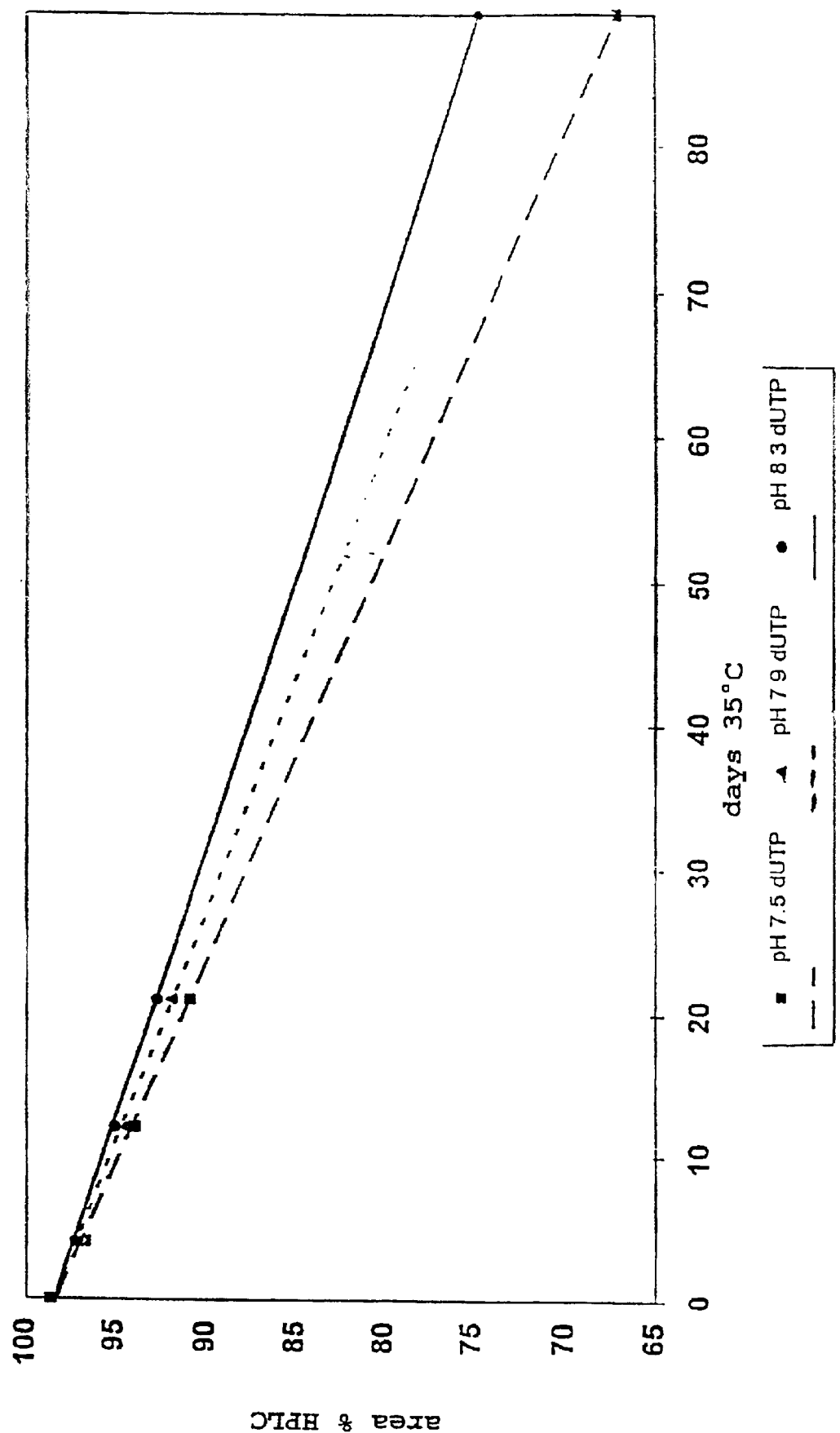

FIG. 4: Decrease of the d-UTP content The decrease of the d-UTP concentration at a temperature of 35° C. was monitored over a period of 90 days at pH values of 7.5, 7.9 and 8.3.

Figure 5:
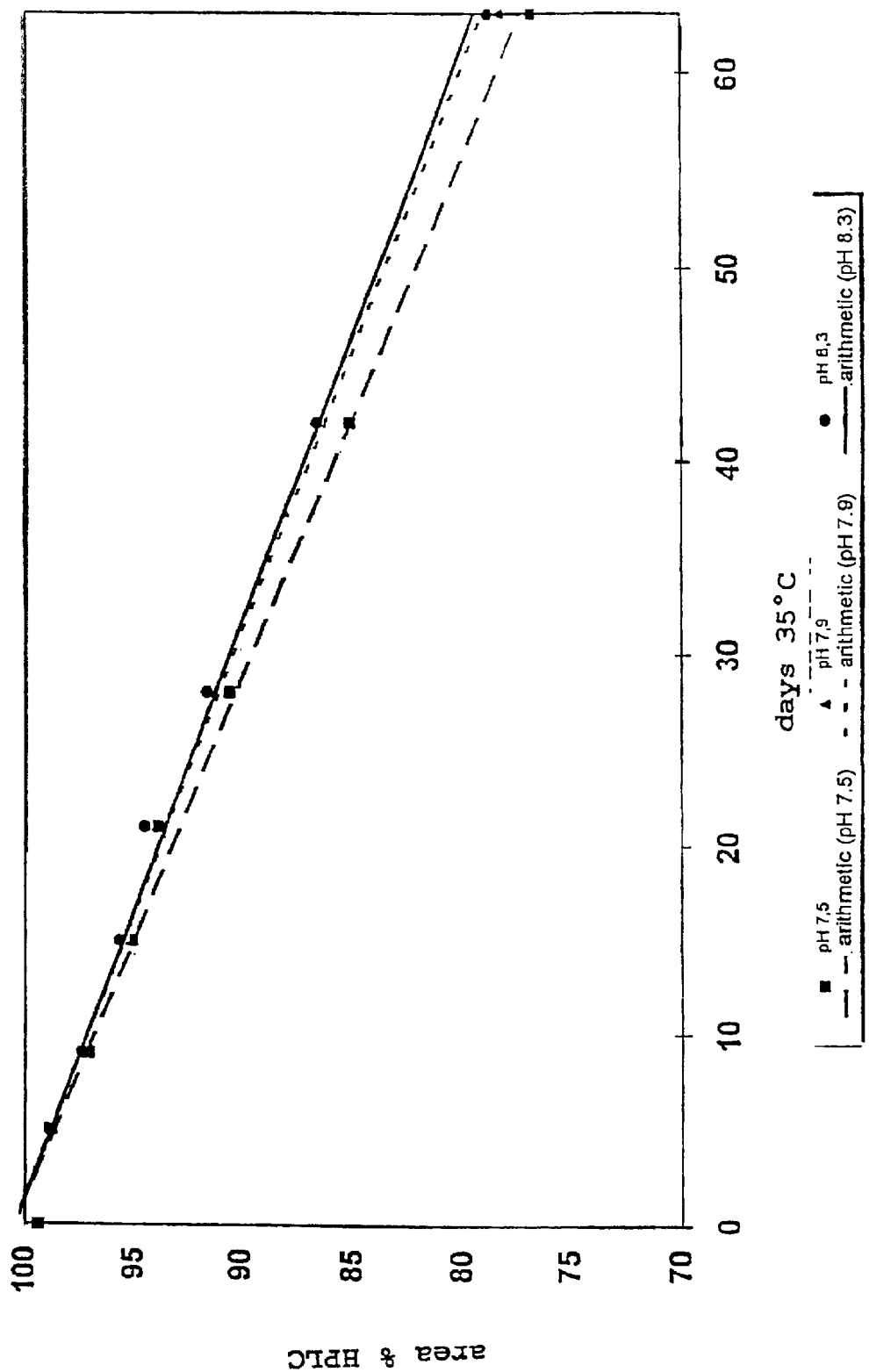

FIG. 5: Decrease of the d-ATP content The decrease of the d-ATP concentration at a temperature of 35° C. was monitored over a period of 65 days at pH values of 7.5, 7.9 and 8.4.

Figure 6:
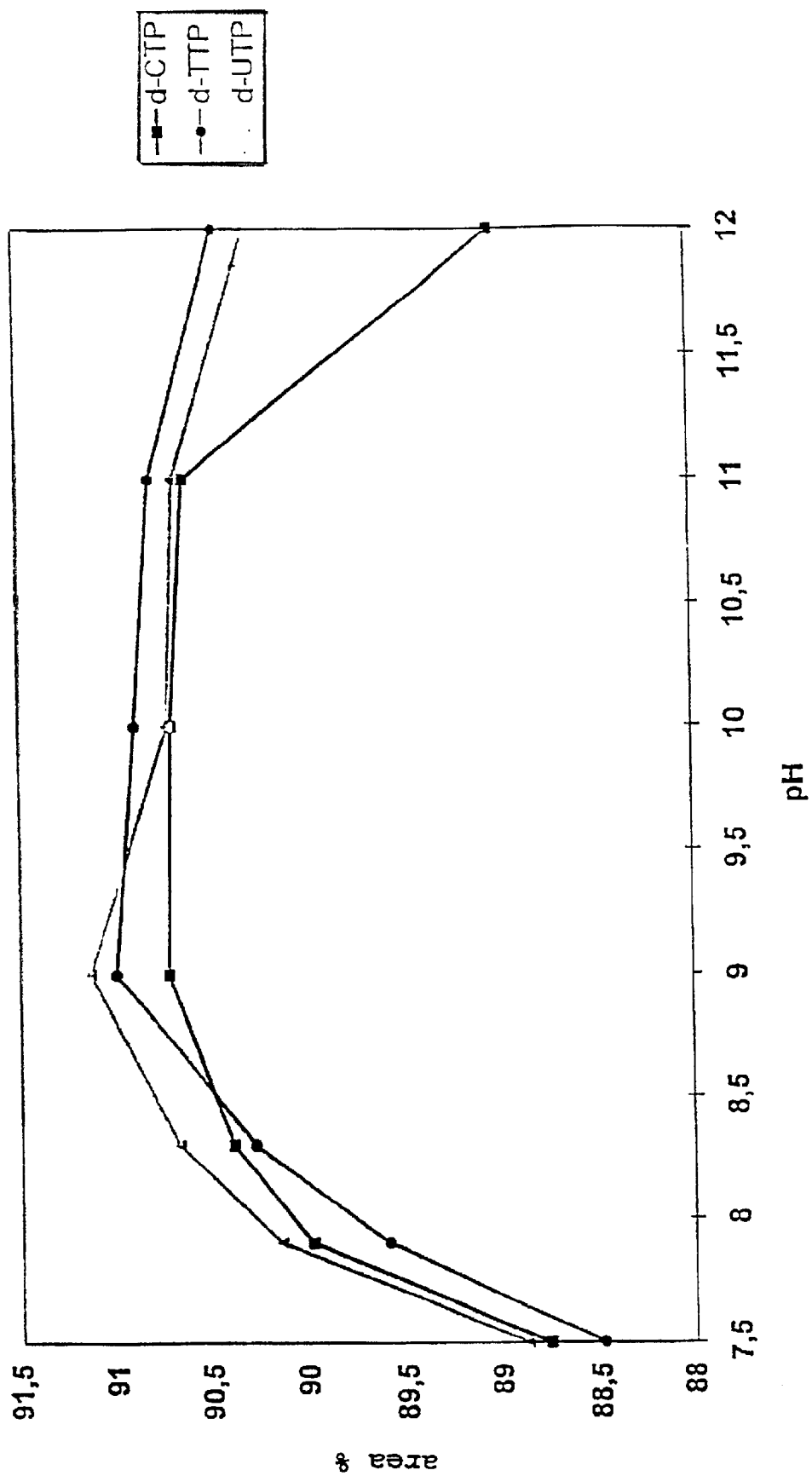

FIG. 6: Triphosphate content in relation to the pH value

Figure 7:
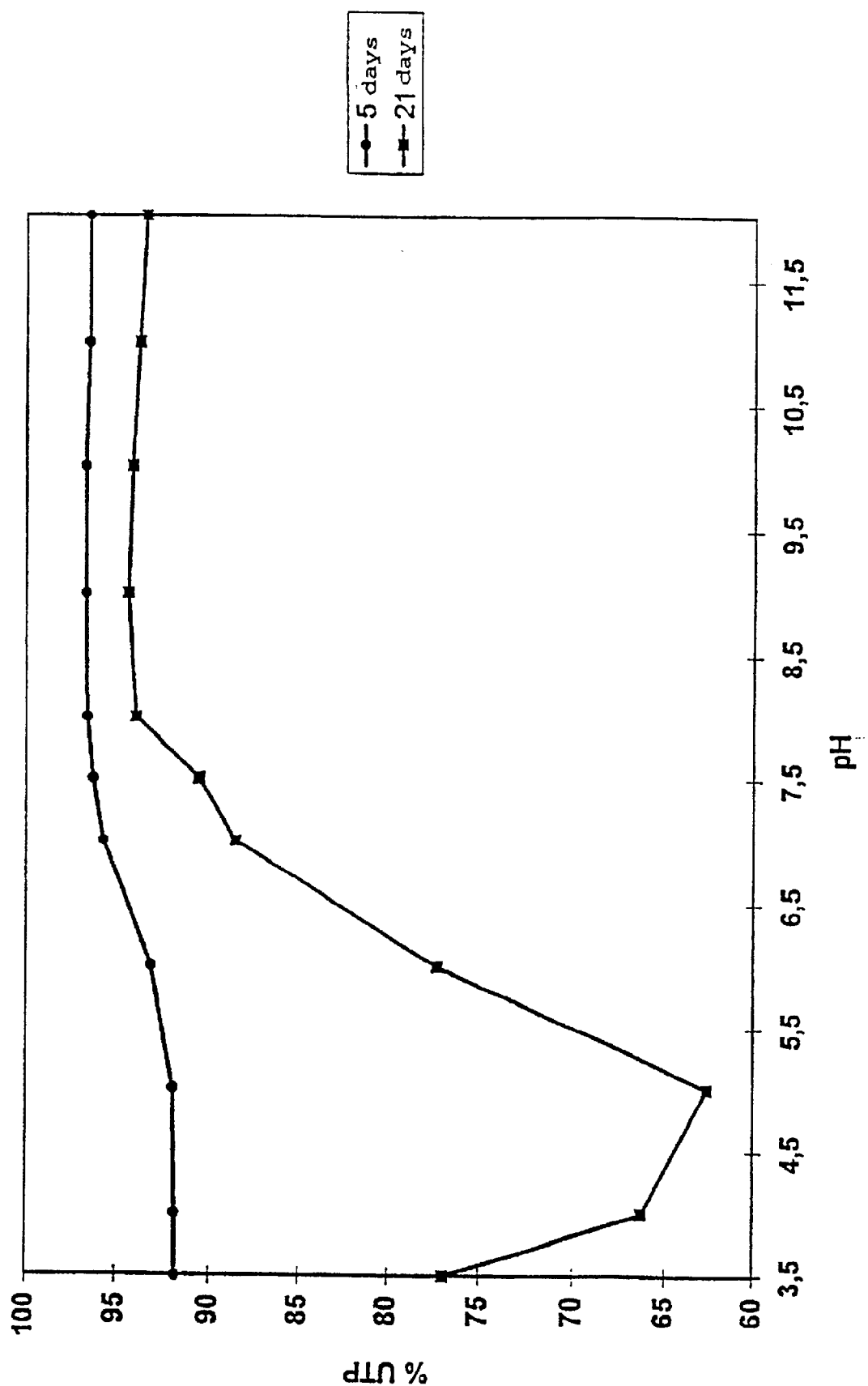

FIG. 7: pH dependence of the stability of UTP

Figure 8:
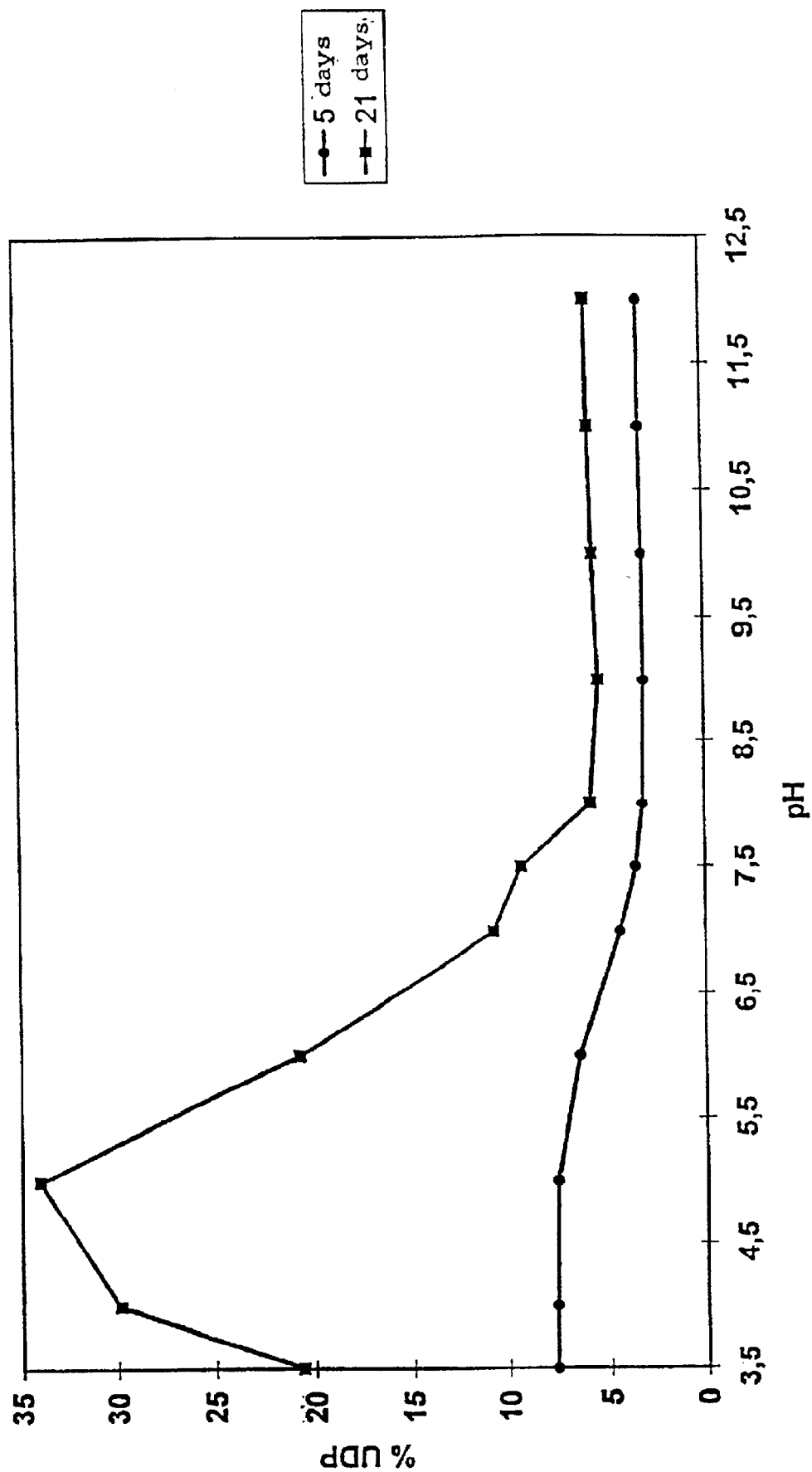

FIG. 8: pH dependence of the stability of UDP

Figure 9:
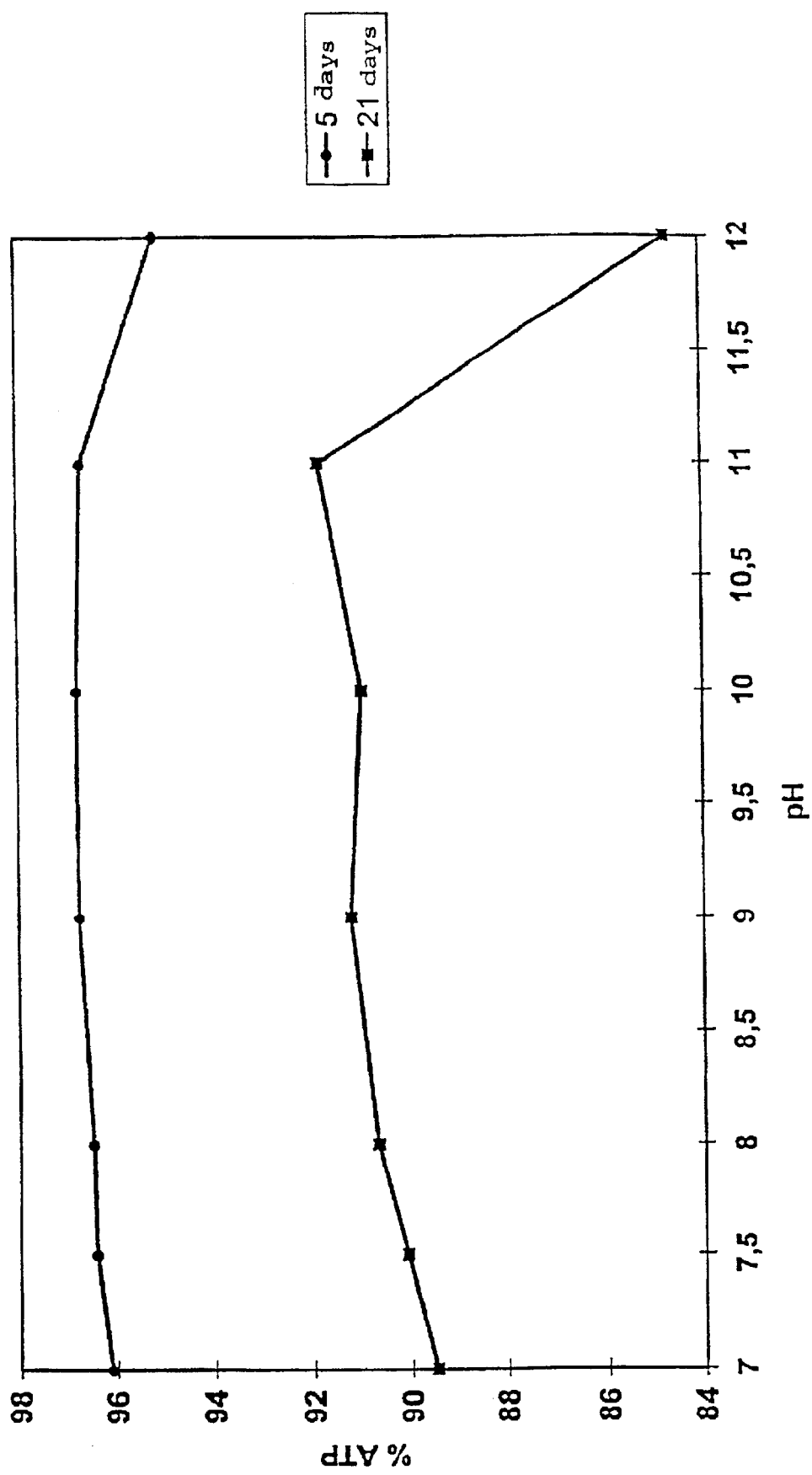

FIG. 9: pH dependence of the stability of ATP

Figure 10:
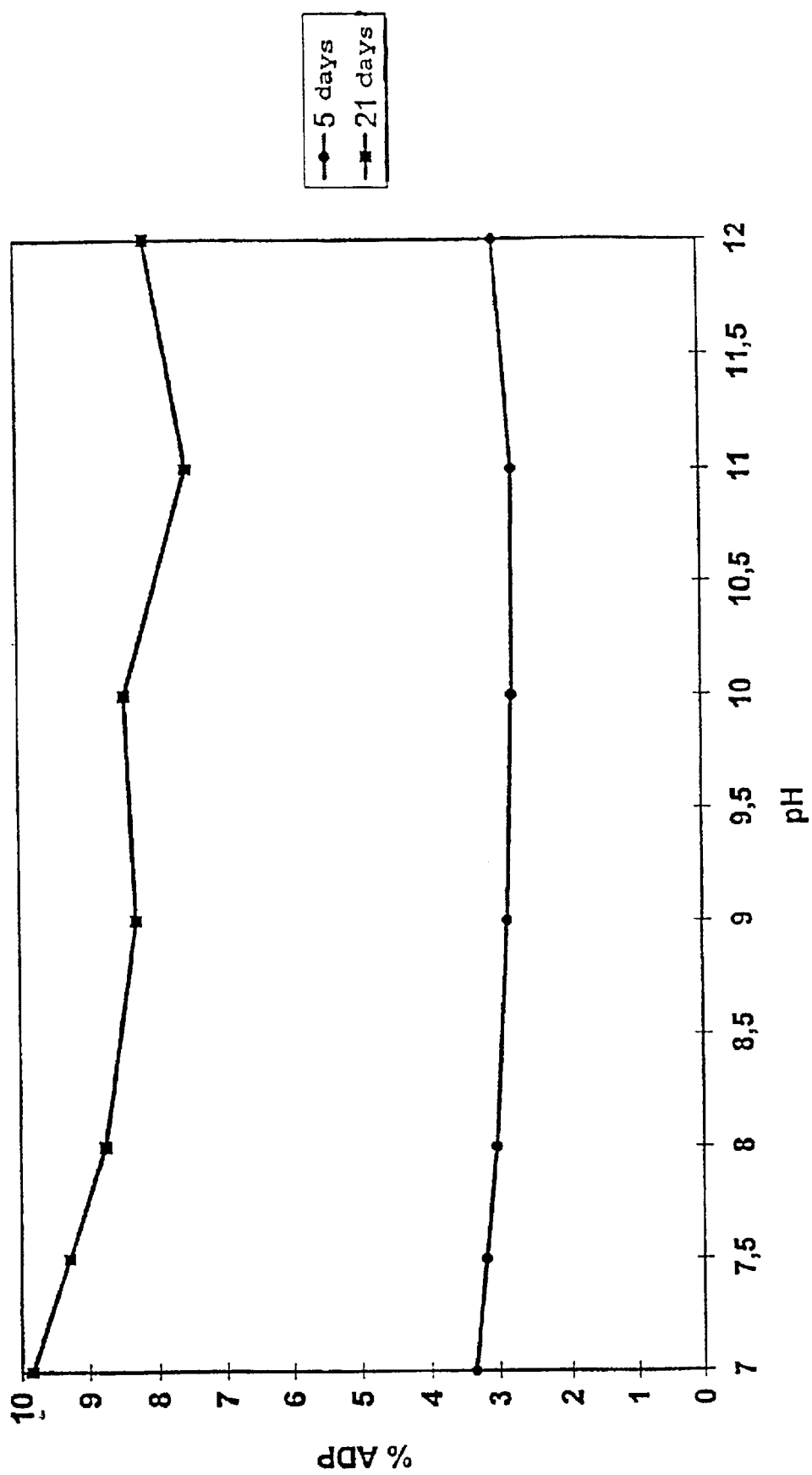

FIG. 10: pH dependence of the stability of ADP

Figure 11:
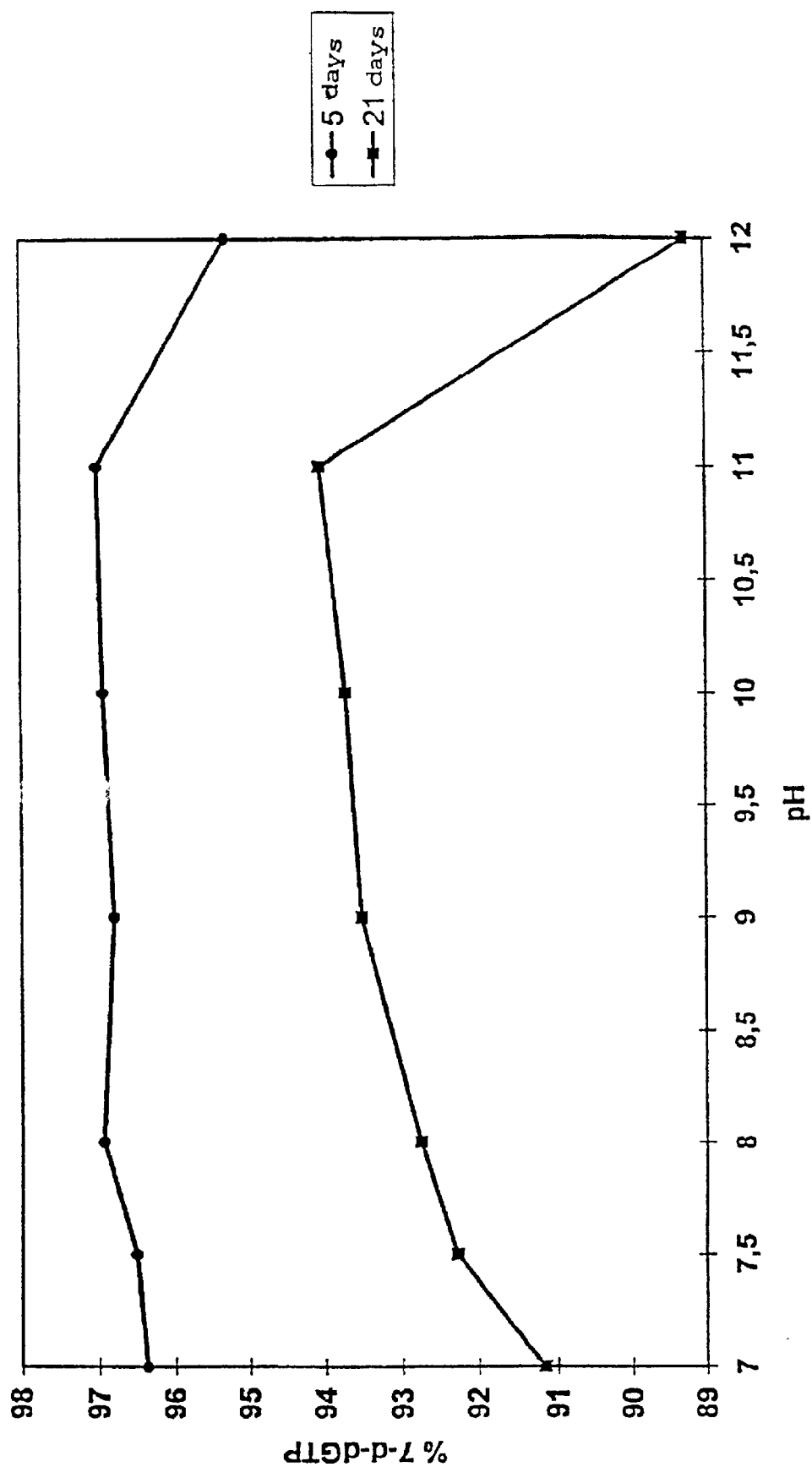

FIG. 11: pH dependence of the stability of 7-deaza-deoxy-GTP

Figure 12:
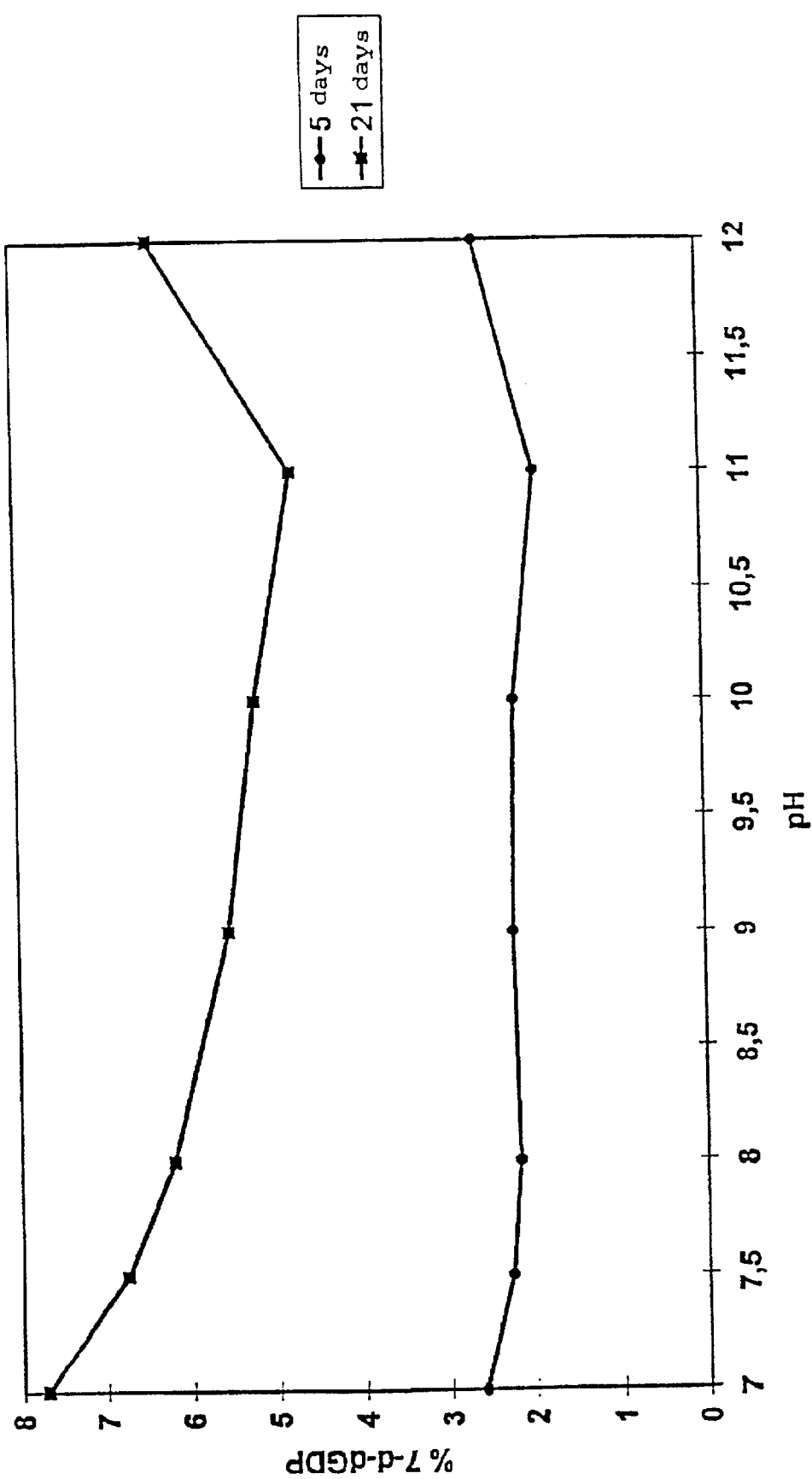

FIG. 12: pH dependence of the stability of 7-deaza-deoxy-GTP

Figure 13:
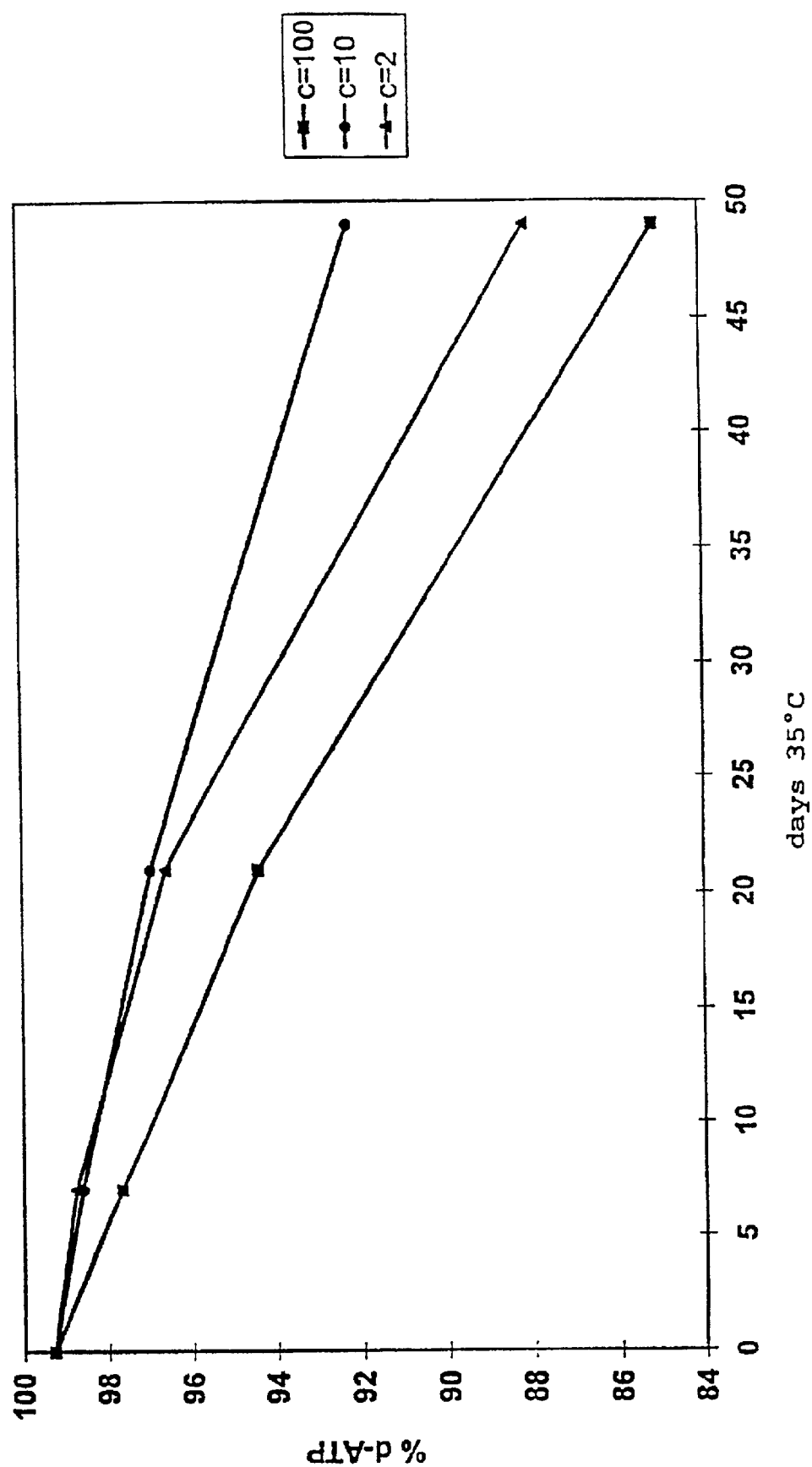
Figure 14:
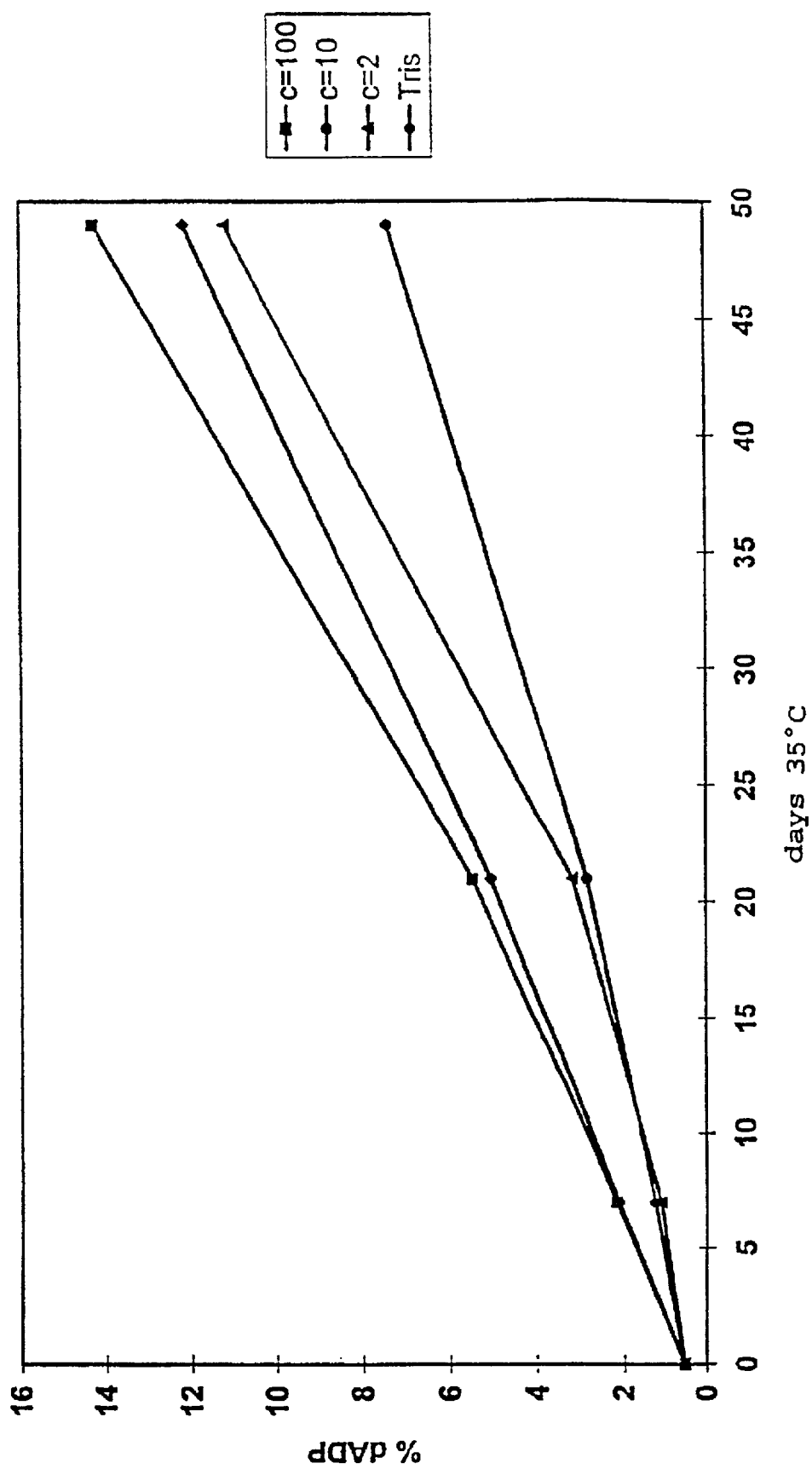
Figure 15:
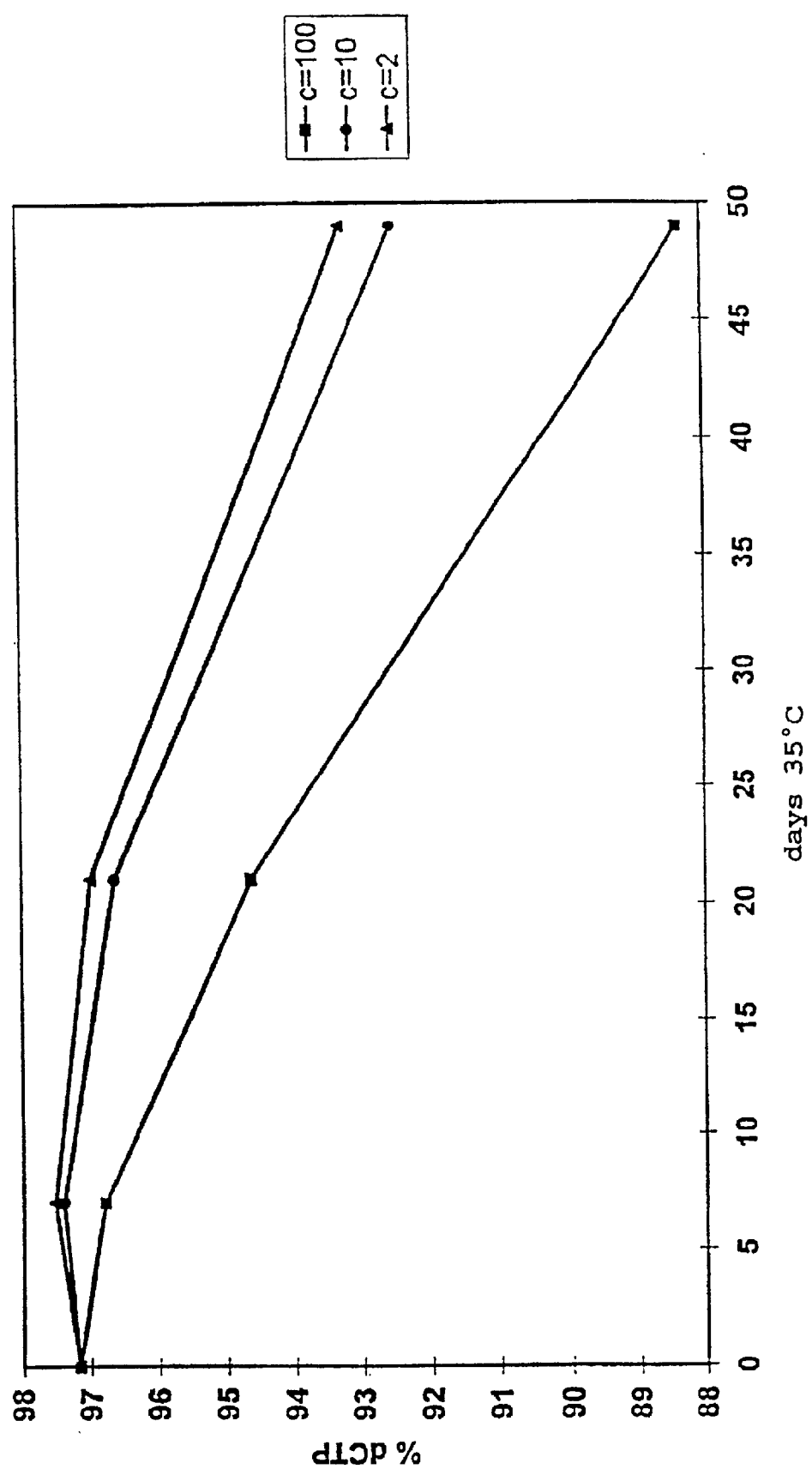

FIG. 13: Dependence of the stability of dATP on the concentration of the solution at pH=8.3, in which c=100 mmol/l, 10 mmol/l and 2 mmol/l FIG. 14: Dependence of the stability of dATP on the concentration of the solution at pH=8.3; in which c=100 mmol/l, 10 mmol/l and 2 mmol/l FIG. 15: Dependence of the stability of dCTP on the concentration of the solution at pH=8.3, in which c=100 mmol/l, 10 mmol/l and 2 mmol/l FIG. 16: Dependence of the stability of dCTP on the concentration of the solution at pH=8.3, in which c=100 mmol/l, 10 mmol/l and 2 mmol/l The invention is further elucidated by the following examples:

EXAMPLE 1
Production of a Stable d-NTP Solution According to the Invention d-NTPs were purified by anion chromatography with the aid of a salt gradient and desalted by reverse osmosis. This is followed by an ultrafiltration (exclusion limit 1000–5000 D) to remove DNAses/RNAses. The concentration of the solution is then adjusted with sterile water to typically 100 mM. The pH value is adjusted to the corresponding pH value (>7.5) by the addition of bases (alkali/alkaline earth/ammonium hydroxide; amines) usually NaOH.

EXAMPLE 2
Degradation of the Triphosphate at Various pH Values d-NTP solutions at a concentration of 100 to 110 mmol/l were adjusted to pH values between 7.5 and 8.3 with sodium hydroxide solution. The sample was stored at 35° C., 22° C., 4° C. and −20° C. Aliquots were removed at various time points and the purity was examined by means of HPLC. The relative amount of the tri, di and monophosphate as well as of the free base was determined by integrating the areas.

The decrease of the triphosphate content is dependent on pH. The decrease was slowest at ca. pH 8.3 for all examined nucleotides (FIGS. 1–5).

I.e. even at higher pH values such as 8.3 no additional peaks are seen in the HPLC chromatogram which could indicate decomposition products.

EXAMPLE 3
Determination of the pH Optimum of the d-NTPs d-NTP solutions (dCTP, dTTP, dUTP) at a concentration of 100 to 110 mmol/l were adjusted to pH values between 7.5 and 12 (d-ATP, dGTP not pH 7.9 and 8.3) with sodium hydroxide solution. The sample was stressed for 35 days at 35° C. and subsequently the purity was examined by means of HPLC. The relative amount of the tri, di and monophosphate as well as of the free base was determined by integrating the areas.

For all examined d-NTPs the optimum was in a range between pH 9.0 and 11.0. Up to pH 12 there was only a slight degradation (except for d-CTP which is deaminated at pH 12 to form d-UTP) (see FIGS. 6, 7, 8, 9, 10, 11, 12).

EXAMPLE 4
Calculation of the Stabilization of d-NTPs at pH 8.3 compared to pH 7.5

The stabilization was estimated by the following formula from three independent stress experiments of d-NTPs at pH 8.3 and 7.5 at 35° C. in which samples were taken at intervals between 7 and 89 days.

$$\Delta \text{ content (pH 8.3)} - \Delta \text{ content (7.5)} \times 100 \, \Delta \text{ content (pH 7.5)}$$

in which $\Delta$ content (pH . . . )=content (t=0)−content (t)

This resulted in the following stabilizations for the individual nucleotides in percent at a pH value of 7.5 compared to a pH value of 8.3 (table 1):

TABLE 1

| Nucleotide | average value | maximum value | minimum value |
|---|---|---|---|
| d-ATP | 19% | 33% | 9% |
| d-CTP | 20% | 37% | 10% |
| d-GTP | 21% | 30% | 12% |
| d-TTP | 5% | 17% | 26% |
| d-UTP | 5% | 15% | 25% |

EXAMPLE 5
Stabilization at Room Temperature

After 204 days (20° C.) the difference in the pH stabilization became apparent (in the real-time model). In the case of d-ATP solutions the triphosphate content for example decreased by ca. 7.6% at pH 7.5, by ca. 6.3% at pH 8.3 (difference 17%). In the case of d-GTP solutions the triphosphate content decreased for example by ca. 6.8% at pH 7.5 and by ca. 5.2% at pH 8.3 (difference 23%).

What is claimed is:

1. An aqueous solution comprising one or more nucleoside triphosphates, wherein the pH value of said solution is between 8 and 10, the concentration of said nucleoside trinphosphates is between 2 to 200 mmol/l, and wherein said solution is free of stabilizing substances.

2. The solution of claim 1, wherein said nucleoside triphosphates are modified nucleoside triphosphates.

3. The solution of claim 1, wherein said nucleoside triphosphates are deoxynucleoside triphosphates.

4. In a method for replicating nucleic acid fragments via a reaction in the presence of an enzyme with reverse transcriptase activity, said method comprising the addition of nucleoside triphosphates to said reaction, the improvement comprising the addition of a solution according to claim 1.

5. In a method for synthesizing nucleic acid sequences via a cycle sequencing reaction, said method comprising the addition of nucleoside triphosphates to said reaction, the improvement comprising the addition of a solution according to claim 1.

6. In a method for random priming of nucleic acid sequences in a reaction, said method comprising the addition of nucleoside triphosphates to said reaction, the improvement comprising the addition of a solution according to claim 1.

7. In a method for nick translation of nucleic acid sequences in a reaction, said method comprising the addition of nucleoside triphosphates to said reaction, the improvement comprising the addition of a solution according to claim 1.

8. In a method for synthesizing nucleic acid sequences via a polymerase chain reaction, said method comprising the addition of nucleoside triphosphates to said reaction, the improvement comprising the use of a solution containing one or more nucleoside triphosphates, wherein the pH value of said solution is between 8 and 10, the concentration of said nucleoside triphosphates is between 2 to 200 mmol/l, and wherein said solution is free of stabilizing substances.

9. An aqueous solution comprising one or more dideoxynucleotide triphosphates, wherein the pH value of said solution is between 8 and 10, the concentration of said nucleoside triphosphates is between 2 to 200 mmol/l, and wherein said solution is free of stabilizing substances.

* * * * *